United States Patent [19]

Hiller

[11] 4,225,584
[45] Sep. 30, 1980

[54] ANIMAL FEEDS CONTAINING A MIXTURE OF NITROVIN, CARBADOX OR OLAQUINDOX AND PROTEOLYTIC ENZYMES

[75] Inventor: Günter Hiller, Erkrath, Fed. Rep. of Germany

[73] Assignee: Henkel Kommanditgesellschaft auf Aktien, Düsseldorf-Holthausen, Fed. Rep. of Germany

[21] Appl. No.: 961,710

[22] Filed: Nov. 17, 1978

[30] Foreign Application Priority Data

Dec. 10, 1977 [DE] Fed. Rep. of Germany ....... 2755126
Jan. 20, 1978 [DE] Fed. Rep. of Germany ....... 2802397

[51] Int. Cl.$^2$ ............................................. A61K 37/48
[52] U.S. Cl. ...................................................... 424/94
[58] Field of Search ............................................ 424/94

[56] References Cited

U.S. PATENT DOCUMENTS

| | | | |
|---|---|---|---|
| 2,878,123 | 3/1959 | Hinsdale et al. | 424/94 |
| 2,906,621 | 9/1959 | Catron | 424/94 |
| 2,988,448 | 6/1961 | Hollenbeck | 424/94 |
| 3,455,696 | 7/1969 | Ukita et al. | 426/43 |
| 3,674,644 | 7/1972 | Yokotsuka et al. | 195/65 |
| 3,677,898 | 7/1972 | Mitsugi et al. | 195/66 R |
| 4,062,732 | 12/1977 | Lehmann et al. | 195/62 |

FOREIGN PATENT DOCUMENTS 46-23622 6/1971 Japan ......................................... 424/94

OTHER PUBLICATIONS

*The Merck Index,* Ninth Edition, (1976), Merck & Co., Inc., Rahway, N.J., U.S.A., 6474 & 1780.

*Primary Examiner*—Frederick E. Waddell
*Attorney, Agent, or Firm*—Hammond & Littell, Weissenberger and Muserlian

[57] ABSTRACT

Animal feeds based on carbohydrates, protein and fats containing from 5 to 350 ppm of one of the growth promoters Nitrovin, Carbadox or Olaquindox and a content of proteolytic enzymes in such an amount that the enzymatic activity is from 0.05 to 2.5 mTU/gm of said animal feed.

17 Claims, No Drawings

ANIMAL FEEDS CONTAINING A MIXTURE OF NITROVIN, CARBADOX OR OLAQUINDOX AND PROTEOLYTIC ENZYMES

BACKGROUND OF THE ART

High-potency animal feeds, as they are normally used today in intensive animal raising, contain a number of additives of prophylactic and/or nutritive effect. These include, among others, antibiotics, growth promoters and enzymes. While the use of antibiotics and/or growth promoters has found acceptance in mixed feeds of all kinds, enzymes are not as yet used on a large scale in the field.

Thus, U.S. Pat. No. 4,062,732 suggest the use of certain acid proteases in feed, and U.S. Pat. No. 3,455,696 suggest the use of procaine penicillin, dehydrostreptomycin or tetracycline and an acid protease in feeds.

The feed mixtures used in modern intensive animal raising programs are generally optimized in all nutrient components to the extent that further improvement does not seem readily possible.

OBJECTS OF THE INVENTION

An object of the present invention is the development of a mixture of growth promoters and enzymes which will improve the present efficiency of animal feeds.

Another object of the present invention is the development of a high efficiency animal feed based on carbohydrates, protein and fats and containing from 5 to 350 ppm of one of the growth promoters Nitrovin, Carbadox or Olaquindox and a content of proteolytic enzymes in such an amount that the enzymatic activity is from 0.05 to 2.5 mTU/gm of said animal feed.

A further object of the invention is the development of a method for efficient rearing of animals comprising feeding animals a high efficiency animal feed based on carbohydrates, protein and fats and containing from 5 to 350 ppm of one of the growth promoters Nitrovin, Carbadox or Olaquindox and a content of proteolytic enzymes in such an amount that the enzymatic activity is from 0.05 to 2.5 mTU/gm of said animal feed.

These and other objects of the invention will become more apparent as the description thereof proceeds.

DESCRIPTION OF THE INVENTION

It has been surprisingly found that even optimally composed high-potency (high efficiency) feeds can be further improved with respect to feed utilization and/or the weight gain attainable therewith by adding to these feeds certain growth promoters together with proteolytic enzymes, particularly acid proteases.

The subject of the invention, accordingly, is an animal feed mixture based on carbohydrates, protein, and fats and optionally the customary additives, characterized by a content of 5 to 350 ppm of one of the growth promoters Nitrovin, Carbadox or Olaquindox and a quantity of proteolytic enzymes such that an enzymatic activity of 0.05 to 2.5 mTU/gm is present.

More particularly, the present invention relates to a high efficiency animal feed based on carbohydrates, protein and fats and containing from 5 to 350 ppm of a growth promoter selected from the group consisting of Nitrovin, Carbadox or Olaquindox and a content of proteolytic enzymes, particularly acid proteolytic enzymes, in such an amount that the enzymatic activity is from 0.05 to 2.5 mTU/gm of said animal feed; as well as a method for efficient rearing of animals comprising feeding animals a high efficiency animal feed based on carbohydrates, protein and fats and containing from 5 to 350 ppm of a growth promoter selected from the group consisting of Nitrovin, Carbadox and Olaquindox and a content of proteolytic enzymes, particularly acid proteolytic enzymes, in such an amount that the enzymatic activity is from 0.05 to 2.5 mTU/gm of said animal feed.

The growth promoter Nitrovin is produced by chemical synthesis. It is 2-[3-(5-nitro-2-furanyl)-1-[2-(5-nitro-2-furanyl)-ethenyl]-2-propenylidene]-hydrazinecarboximid-amide or 1,5-bis-(5-nitro-2-furyl)-1,4-pentadiene-3-one-amidine-hydrazone-HCl (Merck Index, 9th edition, #6474).

The growth promoter Carbadox is likewise produced by chemical synthesis. It is 2-(2-quinoxalinylmethylene)hydrazinecarboxylic acid methyl ester $N^1,N^4$-dioxide or Methyl-3-(2-quinoxalinyl-methylene). The empirical formula is $C_{11}H_{10}N_4O_4$, the molecular weight is 262.23 (Merck Index, 9th edition #1780).

The growth promoter Olaquindox is likewise obtained by chemical synthesis. It is 2-[N-(2-hydroxyethyl)-carbamoyl]-3-methyl-quinoxalin-1,4-dioxide. Its empirical formula is $C_{12}H_{13}N_3O_4$, the molecular weight is 263.3.

Suitable proteolytic enzymes to be employed according to the invention are obtained above all by culturing microorganisms and separation of the enzymes produced from the culture solutions. The processes for this are known. Proteolytic enzymes can be used as produced, for example, from *Bacillus licheniformis, Bacillus natta, Bacillus subtilis*, etc. Especially preferred are acid proteases, e.g., from *Aspergillus niger* or those described in U.S. Pat. Nos. 3,674,644 and 3,677,898. Acid proteases from the genus Tramates or from *Rhizopus rhizopodiformis* according to U.S. Pat. No. 4,062,732 are particularly preferred. Such proteases have a particularly wide spectrum of action in the weakly acid range between pH 2.5 and 6.5. These acid proteases preferably have a pH range of 50% of maximum activity of between a pH of 2.5 and a pH of 6.5.

Commercial feed mixtures are optimally composed for the special needs of the various animal species. They are customarily based on carbohydrates, proteins and fats with optional customary feed supplements or additives. The carbohydrates are chiefly from cereal components, corn or the like. The protein carriers are primarily extracted soybean meal pellets, fish meals, animal body meal, bran and the like. Essential amino acids which are lacking, for example, methionine or lysine, can be added. The fats are employed in the form of plant or animal fats, or added in the form of waste fats. For body building, there are added further salts, such as dicalcium phosphate, calcium carbonate, and common salts. Optionally, the feed mix is balanced by the addition of trace elements, vitamins, ballast substances, etc. Also substances produced fermentatively, such as single cell proteins from petroleum fractions or alcohols, various yeasts, algae protein or others, possibly also substances recovered from waste materials, may be component part of the feed formulation, in part to a considerable degree.

The animal feed mixtures of the invention contain in addition to the usual components adapted for certain animal species or feed use, additionally 5 to 350 ppm, preferably 20 to 50 ppm, depending on the species and age of the animal and the type of feed mix of one of the growth promoters Nitrovin, Carbadox or Olaquindox and the proteolytic enzymes in a quantity such that the enzymatic activity is from 0.05 to 2.5 mTU/gm, preferably 0.2 to 0.5 mTU/gm.

The additive concentrations given above refer to their content in the total feed. In concentrates or supplementary feeds, the concentrations are correspondingly higher. In particular, a combination of one of the above-mentioned growth promoters and an acid fungus protease or respectively protease mixture is employed. The weight gain or, respectively, the improvement in the feed utilization achieved thereby, is up to several percent in comparison with corresponding control mixtures containing only one of the growth promoters.

The active combination of Nitrovin, Carbadox or Olaquindox and proteolytic enzymes is successful especially in feeds for pig raising and hog fattening; as well as in feeds for fattening roosters. However, it can be useful also for all other kinds of animals where the use of growth promoters alone is already of advantage.

At the higher usage levels the active combination of the mentioned growth promoters and enzymes is successful especially in piglet starter and hog fattening feeds.

The growth promoter is expediently added to the feed in the form of a premix, for example, combined with extracted soybean meal pellets. When using mixed meal type feed compositions, the enzyme component is also applied as a premix. Here, as carrier substance, any feed component can be used, for example, again extracted soybean meal pellets. When employing steam-tempered pelletizing of animal feeds, the admixture of the enzymes must occur in suitable stabilized form, to prevent deactivation by moisture and heat during the pelletizing. Such a method is the subject, for example, of U.S. Patent Application Ser. No. 760,358, filed Jan. 19, 1977.

To determine the enzymatic activity of the enzyme unit (TU), the proteolytic activity of the protease is ascertained by the known principle of Anson. A suitable diluted quantity of enzyme solution is incubated for twenty minutes at 40° C. with an equal volume of a 1.2% casein solution, the latter containing 0.6% lactic acid, 6 mols of urea and 0.1 mol of citric or acetic acid. The pH of the casein solution is adjusted to 4.5 by addition of 2 N sodium hydroxide solution. After the incubation, the procedure is to admix with 0.4 N trichloroacetic acid in the volumetric ratio 1:1. The forming precipitate of undigested casein is filtered, and the protein cleavage products formed during degradation are ascertained in the filtrate by any method of protein determination. Suitable for this is, for example, the method described by Layne in Method of Enzymology 3 (1957), pages 448 ff.

For each test sample a blank value must be produced, wherein first trichloroacetic acid and then casein solution is added. This blank value indicates, in addition to the reagent blank value, the proportion of peptides of low molecular weight already present before the digestion in the enzyme solution. The difference between main and blank value is then compared, following the indicated method, with the extinction, which is given by a predetermined amount of tyrosine. This amount of tyrosine is then a measure of the proteolytic activity of the enzyme being determined. The enzyme unit (TU) is that amount of enzyme which releases in one minute from the casein solution the cleavage products which have the same extinction value as a 1 M tyrosine solution. It is customary to express this in $mTU = 10^{-3} TU$.

The following examples are illustrative of the invention without being limitative in any respect.

EXAMPLE 1

240 piglets in the weigh bracket of from about 7 kg to about 22 kg were fed an identically composed raising feed, but which (a) was without addition of growth promoter or enzyme, or (b) was with an addition of 50 ppm of Nitrovin, or (c) with an addition of 50 ppm of Nitrovin and 0.45 mTU/gm of acid proteases from Rhizopus rhizopodiformis and Aspergillus niger.

The animals were kept in flat cages for 7 or 8 animals. Feeding was ad libidum. For habituation an identically composed starter feed was administered to all groups to the above named initial weight. Then the animals received the actual test mixtures as described below with the additives above.

The growth progress and feed utilization were determined by regular weighing. By "feed utilization" is understood the ratio of feed consumption to weight increase.

| Feed composition (%): | |
| --- | --- |
| Protein feed consisting of | |
|   62.5% of extracted soybean meal pellets | |
|   (44% raw protein) | |
|   25% fish meal | 18 |
|   12.5% minerals and vitamin premix | |
| Oats | 14 |
| Wheat bran | 10 |
| Barley | 28 |
| Wheat | 15 |
| Corn | 15 |
| | 100 |

TABLE I

| | Results | | |
| --- | --- | --- | --- |
| | (a) No addition | (b) With Nitrovin | (c) With Nitrovin + enzyme |
| Daily increase (gm) | 380.6 | 412.1 | 444.7 |
| Feed utilization | 2.14 | 2.12 | 2.06 |

EXAMPLE 2

216 piglets in the weight of from about 6.5 kg to about 24.8 were fed an identically composed raising feed, but which (a) was without addition of growth promoter or enzyme, or (b) was with an addition of 50 ppm of Carbadox, or (c) with an addition of 50 ppm of Carbadox and 0.45 mTU/gm of acid proteases from *Rhizopus rhizopodiformis* and Aspergillus.

The animals were kept in flat cages for 7 or 8 animals. Feeding was ad libidum. For hibituation an identically composed starter feed was administered to all groups. Then the animals received the actual test mixtures as described below with the additives above.

By regular weighing the growth progress and the feed utilization were determined. By "feed utilization" is understood the ratio of feed consumption to weight increase.

| Feed composition (%): | |
|---|---|
| Protein feed consisting of: | |
|   62.5% extracted soybean meal pellets (44% raw protein), | |
|   25% fish meal | 18% |
|   12.5% mineral substance and vitamin premix | |
| Oats | 14% |
| Wheat bran | 10% |
| Barley | 28% |
| Wheat | 15% |
| Corn | 15% |
| | 100% |

TABLE II

| | Results | | |
|---|---|---|---|
| | (a) No addition | (b) With Carbadox | (c) With Carbadox + enzyme |
| Daily increase (gm) | 461 | 526 | 543 |
| Feed utilization | 2.11 | 1.98 | 1.91 |

EXAMPLE 3

A total of 48 piglets kept without straw on flat floors were fed from an initial weight of about 30 kg in two fattening stages to the final weight of about 100 kg, with an identically composed feed mix which in Stage I (30 to 60 kg)

(a) was without addition of a growth promoter or enzyme, or (b) was with an addition of 50 ppm of Carbadox, or (c) with an addition of 50 ppm of Carbadox and 0.6 mTU/gm of acid proteases from *Rhizopus rhizopodiformis*.

In fattening stage II (60 to 100 kg) the following additive quantities were used in the corresponding groups:

(a) without addition of a growth promoter or enzyme, or (b) with an addition of 25 ppm of Carbadox, or (c) with an addition of 25 ppm of Carbadox and 0.3 mTU/gm of acid proteases from *Rhizopus rhizopodiformis*.

By regular weighing the growth progress and the feed utilization were determined. By feed utilization is understood the ratio of feed consumption to weight increase. The animals were fed in rations (twice daily) according to the DLG recommendations.

| Feed composition (%) | First fattening 30 to 60 kg | Final fattening 60 to 100 kg |
|---|---|---|
| Barley | 20 | 22 |
| Corn | 20 | 22 |
| Wheat | 15 | 22 |
| Oats | 15 | — |
| Wheat bran | 9 | 21.5 |
| Fish meal | 7 | 3 |
| Extracted soybean meal pellets | 12 | 8 |
| Feed minerals | 2 | 1.5 |

TABLE III

| | Results | | |
|---|---|---|---|
| 30 to 100 kg total fattening | | | |
| | (a) No addition | (b) with Carbadox | (c) With Carbadox + enzyme |
| Daily increase (gm) | 674 | 722 | 753 |
| Feed utilization | 3.31 | 3.18 | 3.14 |

EXAMPLE 4

Groups of 10 piglets in the weight bracket of 11 to 25 kg were fed an identically composed raising feed, but which (a) was without addition of a growth promoter or enzyme, or (b) was with an addition of 30 ppm of Olaquindox, or (c) with an addition of 30 ppm of Olaquindox and 0.5 mTU/gm of acid proteases from *Aspergillus niger*.

The test took place on a straw scattered floor. Feeding was ad libitum. In analogy with the method mentioned in Examples 2 and 3, the daily weight increase and the feed utilization was determined.

| Feed composition (%): | |
|---|---|
| Barley | 15 |
| Oats | 15 |
| Corn | 20 |
| Wheat | 10 |
| Wheat bran | 17 |
| Alfalfa meal | 2 |
| Extracted soybean meal pellets | 12 |
| Fish meal | 6 |
| Feed minerals | 3 |
| | 100 |

TABLE IV

| | Results | | |
|---|---|---|---|
| | (a) Without addition | (b) With Olaquindox | (c) With Olaquindox + enzyme |
| Daily increase (gm) | 492 | 530 | 557 |
| Feed utilization | 2.05 | 2.04 | 2.00 |

EXAMPLE 5

In analogy to the conditions of Example 3, identical feed mixtures were fed to groups of 8 hogs in the weight bracket of 30 to 100 kg, but which, (a) were without addition of a growth promoter or enzyme, or (b) with an addition of 80 ppm of Olaquindox, or (c) with an addition of 80 ppm of Olaquindox and 0.6 mTU/gm of acid proteases from *Aspergillus niger* and *Rhizopus rhizopodiformis*.

The concentrations of said additives remained unchanged during the entire fattening period. Feeding methods and feed composition corresponded to Example 3.

TABLE V

| | Results | | |
|---|---|---|---|
| | (a) Without addition | (b) With Olaquindox | (c) With Olaquindox + enzyme |
| Daily increase | 640 | 671 | 696 |

TABLE V-continued

| | Results | | |
|---|---|---|---|
| | (a) Without addition | (b) With Olaquindox | (c) With Olaquindox + enzyme |
| (gm) Feed utilization | 3.27 | 3.19 | 3.13 |

EXAMPLE 6

1800 Lohmann-B 975 fattening roosters kept on floors were fed for 6 weeks with identically composed feed mixtures, but (a) without addition of growth promoter or enzyme, or
(b) with addition of 15 ppm of Nitrovin, or
(c) with addition of 15 ppm of Nitrovin and 0.65 mTU/gm of acid proteases from *Aspergillus niger* and *Rhizopus rhizopodiformis* and after conclusion of the test the end weight of the animals and the feed utilization were determined. By feed utilization is understood the ratio of feed consumption to weight increase.

| Feed composition (%): | |
|---|---|
| Extracted soybean meal pellets (50%) | 36.96 |
| Corn | 32.53 |
| Corn starch | 17.05 |
| Soybean oil | 6.5 |
| Feed calcium phosphate | 2.01 |
| Feed calcium carbonate | 0.95 |
| NaCl | 0.36 |
| Methionine | 0.21 |
| Vitamin mixture | 0.25 |
| Choline chloride | 0.25 |
| Trace elements | 0.05 |
| Coccidiostatic | 0.05 |
| Oat husks | 2.83 |
| | 100.00 |

TABLE VI

| | Results | | |
|---|---|---|---|
| | (a) No addition | (b) With Nitrovin | (c) With Nitrovin + enzymes |
| Increase (gm) | 1454 | 1581 | 1580 |
| Feed utilization | 1.81 | 1.77 | 1.74 |

The preceding specific embodiments are illustrative of the practice of the invention. It is to be understood, however, that other expedients known to those skilled in the art or disclosed herein may be employed without departing from the spirit of the invention or the scope of the appended claims.

I claim:

1. A high efficiency animal feed based on carbohydrates, protein and fats and containing from 5 to 350 ppm of a growth promoter selected from the group consisting of Nitrovin, Carbadox and Olaquindox and a content of proteolytic enzyme selected from the acid proteases from *Aspergillus niger* or *Rhizopus rhizopodiformis*, or a mixture thereof, in such an amount that the enzymatic activity is from 0.05 to 2.5 mTU/gm of said animal feed.

2. The animal feed of claim 1 wherein said proteolytic enzyme is an acid protease with a wide spectrum of action in the range of between a pH of 2.5 and 6.5.

3. The animal feed of claim 2 wherein said acid protease has a pH range of 50% of maximum activity of between a pH of 2.5 and a pH of 6.5.

4. The animal feed of claim 1 wherein said enzymatic activity is from 0.2 to 0.5 mTU/gm of said animal feed.

5. The animal feed of claim 1 wherein said growth promoter is Nitrovin and is present in an amount of from 15 to 50 ppm.

6. The animal feed of claim 1 wherein said growth promoter is Carbadox and is present in an amount of from 20 to 50 ppm.

7. The animal feed of claim 1 wherein said growth promoter is Olaquindox and is present in an amount of from 20 to 80 ppm.

8. A method for efficient rearing of animals comprising feeding animals a high efficiency animal feed based on carbohydrates, protein and fats and containing from 5 to 350 ppm of a growth promoter selected from the group consisting of Nitrovin, Carbadox and Olaquindox and a content of proteolytic enzyme selected from the acid proteases from *Aspergillus niger* or *Rhizopus rhizopodiformis*, or a mixture thereof, in such an amount that the enzymatic activity is from 0.05 to 2.5 mTU/gm of said animal feed.

9. The method of claim 8 wherein said proteolytic enzyme is an acid protease with a wide spectrum of action in the range of between a pH of 2.5 and 6.5.

10. The method of claim 9 wherein said acid protease has a pH range of 50% of maximum activity of between a pH of 2.5 and a pH of 6.5.

11. The method of claim 8 wherein said enzymatic activity is from 0.2 to 0.5 mTU/gm of said animal feed.

12. The method of claim 8 wherein said growth promoter if Nitrovin and is present in an amount of from 15 to 50 ppm.

13. The method of claim 8 wherein said growth promoter is Carbadox and is present in an amount of from 20 to 50 ppm.

14. The method of claim 8 wherein said growth promoter is Olaquindox and is present in an amount of from 20 to 80 ppm.

15. The method of claim 8 wherein said animals are pigs.

16. The method of claim 8 wherein said animals are roosters.

17. A method for improving the growth producing characteristics of an animal feed which comprises adding thereto from 5 to 350 ppm of a growth promoter selected from the group consisting of Nitrovin, Carbadox and Olaquindox and an amount of proteolytic enzyme selected from the acid proteases from *Aspergillus niger* or *Rhizopus rhizopodiformis*, or a mixture thereof, such that the enzymatic activity is from 0.05 to 2.5 mTU/gm of said animal feed.

* * * * *